US011717620B2

(12) United States Patent
Bartels et al.

(10) Patent No.: US 11,717,620 B2

(45) Date of Patent: Aug. 8, 2023

(54) FLEXIBLE PUMPING CHAMBER

(71) Applicant: Softhale NV, Diepenbeek (BE)

(72) Inventors: Frank Bartels, Hattingen (DE); Jürgen Rawert, Cologne (DE)

(73) Assignee: SOFTHALE NV, Diepenbeek (BE)

( * ) Notice: Subject to any disclaimer, the term of this patent is extended or adjusted under 35 U.S.C. 154(b) by 386 days.

(21) Appl. No.: 16/955,798

(22) PCT Filed: Dec. 22, 2018

(86) PCT No.: PCT/EP2018/086833

§ 371 (c)(1),
(2) Date: Jun. 19, 2020

(87) PCT Pub. No.: WO2019/122450

PCT Pub. Date: Jun. 27, 2019

(65) Prior Publication Data

US 2021/0106773 A1 Apr. 15, 2021

Related U.S. Application Data

(60) Provisional application No. 62/610,081, filed on Dec. 22, 2017.

(30) Foreign Application Priority Data

Dec. 22, 2017 (EP) .................................... 17210398

(51) Int. Cl.
*A61M 11/00* (2006.01)
*A61M 15/00* (2006.01)

(52) U.S. Cl.
CPC ...... *A61M 11/007* (2014.02); *A61M 15/0013* (2014.02); *A61M 15/0065* (2013.01); *A61M 2202/0007* (2013.01)

(58) Field of Classification Search
CPC ............ A61M 11/007; A61M 15/0013; A61M 15/0065; A61M 2202/0007;
(Continued)

(56) References Cited

U.S. PATENT DOCUMENTS 4,079,865 A 3/1978 Kutik
4,615,467 A * 10/1986 Grogan ................. B05B 11/043 239/327
4,775,079 A * 10/1988 Grothoff ............. B05B 11/0059 222/402.19

(Continued)

FOREIGN PATENT DOCUMENTS

EP 0689877 A2 1/1996
EP 0627230 B1 2/2000

OTHER PUBLICATIONS

Written Opinion of the International Application No. PCT/EP2018/086833, dated Mar. 4, 2019, 5 pages.

*Primary Examiner* — Timothy A Stanis
*Assistant Examiner* — Matthew R Moon
(74) *Attorney, Agent, or Firm* — Pharma Patents International AG; Lily Ackerman

(57) ABSTRACT

The invention relates to the field of inhalation devices for liquids. In particular, the invention relates to a pumping chamber for such an inhalation device. A pumping unit for an inhalation device for medically active liquids for generation of an aerosol comprises a tubular member (1), a check valve (2), and a counter piece, said counter piece being configured to receive at least a downstream segment of said tubular member (1) and having an interior volume, wherein upstream of said tubular member (1), a reservoir (4) can be fluidically connected with said tubular member (1), and downstream of said counter piece, a nozzle unit (6) can be fluidically connected with said counter piece, and wherein the tubular member (1) comprises an upstream section, a downstream section, and the check valve (2) which is positioned between the upstream section and the down-
(Continued)

stream section, such that a pumping chamber with a pumping chamber volume is defined which comprises the volume of the downstream section of the tubular member (1) and said interior volume of the counter piece, and wherein tubular member (1) and the counter piece can move relatively to one another, such that the pumping chamber volume is variable. The tubular member (1) comprises at least two mechanically distinct parts (1A, 1B), wherein a first part (1A) provides said upstream section, and a second part (1B) provides said downstream section, and the first part (1A) and the second part (1B) are connected to each other such as to form an interface section (1C) serving as a valve chamber (2B) for the valve (2).

6 Claims, 2 Drawing Sheets

(58) Field of Classification Search
CPC .... A61M 2205/073; A61M 2205/8281; B05B 11/3067; B05B 11/3091
See application file for complete search history.

(56) References Cited

U.S. PATENT DOCUMENTS

| | | | | |
|---|---|---|---|---|
| 5,388,766 | A * | 2/1995 | Buisson | B05B 11/3014 222/321.2 |
| 6,189,739 | B1 | 2/2001 | Von Schuckmann | |
| 2004/0068222 | A1* | 4/2004 | Brian | A61M 11/002 604/152 |
| 2011/0084100 | A1 | 4/2011 | Welp | |

* cited by examiner

FLEXIBLE PUMPING CHAMBER

CROSS REFERENCE TO RELATED APPLICATIONS

This application is a United States National Stage Application filed under 35 U.S.C. § 371 claiming priority to and the benefit of PCT Application No. PCT/EP2018/086833, filed on Dec. 22, 2018, which claims priority to and the benefit of European Application No. 17210398.8, filed on Dec. 22, 2017, and U.S. Provisional Application Ser. No. 62/610,081, filed on Dec. 22, 2017, all of which are incorporated herein by reference in their entireties.

FIELD OF THE INVENTION

The invention relates to the field of inhalation devices for liquids. In particular, the invention relates to a pumping chamber for such an inhalation device.

BACKGROUND OF THE INVENTION

Nebulizers or other aerosol generators for liquids are known from the art since a long time ago. Amongst others, such devices are used in medical science and therapy. There, they serve as inhalation devices for the application of active ingredients in the form of aerosols, i.e. small liquid droplets embedded in a gas. Such an inhalation device is known e.g. from document EP 0 627 230 B1. Essential components of this inhalation device are a reservoir in which the liquid that is to be aerosolized is contained; a pumping unit for generation of a pressure being sufficiently high for nebulizing; as well as an atomizing device in the form of a nozzle.

Typically, the inhalation device comprises also a pipe which is fluidically connected with its first, upstream end to said reservoir, and with its second, downstream end to said pumping unit. A valve, e.g. a ball valve, which is contained in the pipe ensures that the flow of liquid can only occur in the desired direction, i.e. from the reservoir to the pumping unit and the nozzle.

The so called pumping chamber is the volume where the liquid is collected and pressurized for emission through the nozzle. The volume of the pumping chamber consists of the pipe's interior volume downstream the valve, and the volume of a pumping unit's opening into which the pipe can be inserted during pumping action.

For pumping, and therefore, pressure generation, the pipe is firstly pulled out of the pumping device, such that the overall volume of the pumping chamber increases. The resulting negative pressure inside the chamber leads to the sucking in of liquid from the reservoir through the valve into the pumping chamber. When the chamber has reached its maximum volume, the motion can now be reversed. The valve blocks any back flow of liquid into the reservoir, and therefore, a positive pressure builds up inside the pumping chamber, since the nozzle as the only outlet has a relatively high fluidic resistance. The liquid is forced out of the downstream end of the pumping device, into the nebulizing structure of the nozzle. Once the chamber has reached its minimum volume, an entire dose is delivered. Now, refilling of the chamber can start again. It is clear that by adjusting the travel length and diameter of the pipe, the dosing volume of liquid can be adjusted.

In known devices, the pipe is constructed as a hollow tube made of metal having very precise dimensions. Such precision is necessary since otherwise, sealing problems might occur. Further, the ball valve is located inside said tube at a predefined longitudinal position close to a downstream end section of the tube. It is kept in place by a precisely formed wall structure that allows for a certain longitudinal travel within the tube, without letting the ball leaving said end section (cage).

The manufacture of the tube with the necessary precision is costly. Further, if the dosing volume must be adjusted, or if a change of e.g. viscosity of the liquid makes an adjustment of flow resistance, and thus, of the diameter of the tube, necessary, such adjustment is also both a complex and costly measure.

OBJECT OF THE INVENTION

The object of the invention is the provision of a device that avoids the drawbacks of the known art.

The invention reduces the cost of the pumping unit. Further, the invention facilitates the adjustment of the fluidic parameters of the pumping unit with respect to pumping volume or to the fluidic parameters of the liquid.

DESCRIPTION OF THE INVENTION

The object is solved by a device according to claim 1. Advantageous embodiments are described in the dependent claims, the subsequent description, as well as the accompanying figures.

The invention relates to a pumping unit for an inhalation device for medically active liquids for generation of an aerosol. Preferably, the inhalation device is a soft mist inhaler having a pumping unit designed for a high working pressure of e.g. 100 bar or more. The pumping unit comprises a tubular member, a check valve, and a counter piece. The counter piece is configured to receive at least a downstream segment of said tubular member. This member can e.g. be a pipe, a hose or the like. Preferably, it is made of a substantially rigid material. The counter piece has an interior volume which is configured to receive liquid.

Upstream of said tubular member, a reservoir can be fluidically connected with said member, and downstream of said counter piece, a nozzle unit can be (directly or indirectly) fluidically connected. In order to ensure unidirectional flow of the liquid, a check valve is present which is positioned between an upstream section and a downstream section. A pumping chamber with a pumping chamber volume is defined which comprises the volume of the downstream section of the tubular member, starting at the valve, and optionally the interior volume of the counter piece, at least up to the position of a further optional valve accommodated in the counter piece. If the upstream end of the counter piece is inserted in the downstream segment of the tubular member, and if the optional (further) valve is positioned at the very upstream end of the counter piece, the interior volume of the counter piece will obviously not contribute to the pumping chamber volume.

On the other hand, it is also clear that the volume of the walls of the downstream section of the tubular member, if the same is contained in an opening of the counter piece, must be subtracted from the volume of the pumping chamber.

Tubular member and counter piece can move relatively to one another, such that the pumping chamber volume is variable. This pumping principle is a common principle, and can effectively be used for generating sufficiently high pressures within the pumping chamber when the tubular member is moved further towards the counter piece, reducing the volume available for the liquid.

According to the invention, the tubular member comprises at least two mechanically distinct parts (and not only sections of one integral part). This means that prior to a first operation, the tubular member must be assembled from (at least) two separate parts. The first part provides said upstream section, and the second part provides said downstream section. Further, the first part and the second part are connected to each other such as to form an interface section serving as a valve chamber for the aforementioned check valve.

As will be shown in more detail further down, the design of the tubular member in two distinct parts with the valve chamber at the end of the first, or at the beginning of the second part, has a number of advantages. In short, the construction becomes more simple, and can be carried out with less precision. Moreover, the design makes the assembly of the pumping unit easier.

In particular, only the second part which comes in contact with the counter piece must be of higher precision, whereas the first part which contacts the reservoir can be of a lower precision. Further, since the section which houses the valve, i.e. the valve chamber, is easily accessible, it is easier to manufacture that region with sufficiently high precision in order to obtain a well working check valve. Also, installation of the valve becomes much easier. Further on, the invention allows for more flexibility regarding the design and size of the valve chamber. From assembling, it is sufficient to press both parts together after inserting moveable parts of the valve. Also, if the fluidic characteristics of the pumping unit must be adjusted, only the second part must be exchanged, whereas the first part and the valve can be left unchanged.

According to a preferred embodiment, the counter piece comprises a riser pipe which extends towards the second part of the tubular member and which is at least partially insertable into the second part of the tubular member. This means that a hollow, pipe-like member is present which has an outer diameter that matches the inner diameter of the second part of the tubular member. Thus, the latter can slide onto and along the first until motion is blocked e.g. by the valve reaching the upstream end of the riser pipe, or the downstream end of the tubular member reaching the downstream end of the counter piece.

In another embodiment, the counter piece comprises an opening, said opening being configured to receive at least part of the downstream section of said tubular member. This means that the tubular member can partially "dive" into the opening, the inner diameter of which matching the outer diameter of the second part of the tubular member.

In both cases, the resulting pumping chamber volume will decrease when the tubular member is further approaching the counter piece, and vice-versa. It is noted that also a combination of both embodiments is possible.

According to one embodiment, the outside diameter of both parts (first and second part) is substantially identical. This means that the outside of the entire tubular member has substantially the same size. Such a construction allows for a very long travel distance of the tubular member into the opening or over the riser pipe, respectively, since there is no obstacle restraining the motion of the tubular member. Further, only one type of tubes or pipes must be held available for manufacture.

In another embodiment, the outside diameters of both parts differ from one another. As will be shown, a larger diameter of the section which houses the valve chamber allows for greater flexibility with regard to the design of said chamber and valve. Also, since the pressure in the first part is significantly lower than in the second part (only the second part belongs to the pumping chamber), the first part must withstand lower forces and can therefore have e.g. a thinner wall that the second part.

In another embodiment, the valve chamber has a lateral wall, and a section of that part which forms or houses the lateral wall of the valve chamber has an increased diameter with respect to (i) the rest of this part, or (ii) the other part. In both cases, a larger space for the interface section, and thus, more space for the valve is provided. At least, the internal diameter is increased, but preferably, the external diameter is increased as well in order not to weaken the respective walls.

In case (i), the part which houses that valve chamber has a locally enlarged diameter. This allows for providing a larger (wider) valve chamber.

In case (ii), the entire part (first or second part) has a larger diameter than the other part. In this case as well, more space for the valve chamber is available, and a part of substantially identical diameter can be easier to manufacture than a part which has only local sections of a wider diameter. However, on the other hand, a construction according to (i) uses less space which can be crucial in some applications.

In other embodiments, the inner diameter of the valve chamber can be decreased. In certain applications, a smaller and therefore faster moveable part can be advantageous.

In one embodiment, the part which does not form or comprise the lateral wall of the valve chamber has at its upstream end a structure for holding back a moveable part of the valve. Such a structure has the task of "closing" the valve chamber such that e.g. the ball (of a ball check valve) stays inside the valve chamber. This is achieved in providing a structure that has a clear diameter which is smaller than the diameter of the ball. Of course, other valve types are possible as well, such as flap valves and the like. However, also in these cases, the valve chamber can be closed by a comparable structure that allows motion of the moveable part of the valve, but ensures that said part is not leaving the valve chamber.

In one embodiment, said structure for retaining the moveable part of the valve within the valve chamber is provided by a reduced interior diameter of said (first or second) part. That means that the part which does not provide the valve chamber has an at least partially reduced interior diameter which is smaller than the diameter of the ball (in case of a ball valve). Thus, the ball cannot enter the interior of said part.

In another embodiment, said structure is provided by a surface inside said part with at least two through holes. In other words, the part provides a sieve like structure which closes the valve chamber for the moveable part, but which lets liquid pass.

The advantage of both embodiments is that, due to the two part design, both described structures can be manufactured rather easily. Since the structure is arranged at the respective end of the first, or the beginning of the second part, it is well accessible, and thus, machinable.

In one of the preferred embodiments, the valve chamber is provided by the second part. By locating the valve chamber in the second part, the subsequent advantages can be achieved. In this context, the part which provides the lateral wall or which contains most of the valve components is considered as the part providing the valve chamber.

Firstly, in such a case, the first and the second part can advantageously be made of different materials. Although this is possible in other cases as well, in the case when the valve chamber is provided by the second part, the first part can be made of a weaker material than the second part, because only the second part is exposed to high pressures. The first part does not hold any high pressure sections, since only the second part houses sections downstream the moveable part of the valve, and only these sections are exposed to said high pressures.

As a result, costly material can be saved, reducing the cost of the pumping unit. Also, processing of weaker materials is usually easier and quicker, again resulting in a reduction of costs.

Secondly, to the first part of the tubular member, easily more than one reservoir can be fluidically connected, such that mixing of the different liquids in the valve chamber can occur. In other words, when the valve chamber is not provided by the first part, in turn, said part provides more design freedom with respect to the “inlets” which connect the valve chamber via said first part to one or even more reservoirs. A “Y” shaped downstream end of the first part can be provided to connect to two reservoirs, and as a result, the valve chamber serves at the same time as a mixing chamber for these liquids. Due to the turbulences to which the liquids are exposed when entering, passing and leaving the valve chamber, it serves as an ideal (pre-)mixing chamber.

It is of course also possible to provide more than one fluidic connection to the valve chamber when the latter is provided in the first part. However, the aforementioned embodiment is preferred, since the separation of functions leads to a more simple and thus less costly construction.

The invention relates also to an inhalation device for medically active liquids for generation of an aerosol, the device comprising a pumping unit according to the above description. In order to avoid repetitions, reference is made to said description. An inhalation device, comprising said pumping unit, provides a number of advantages; in particular, it can be manufactured at reduced costs and it can be more easily be adapted to varying fluidic properties of different liquids.

Further, the invention relates to a tubular member for a pumping unit for an inhalation device for medically active liquids for generation of an aerosol; the tubular member is defined as described herein-above in the context of the disclosure of the pumping unit comprising such tubular member. Such a tubular member is easier to manufacture than previously known tubular members that have a similar functionality. Moreover, the tubular member according to the present invention provides greater flexibility with regard to adaptation for a broad range of fluidic parameters, doses, and necessary space.

DESCRIPTION OF FIGURES

In FIG. 1, a schematic cut view of an inhalation device is shown. The figure shows the general arrangement of a pumping unit in an inhalation device, but without showing all features of the invention.

Figure 1:
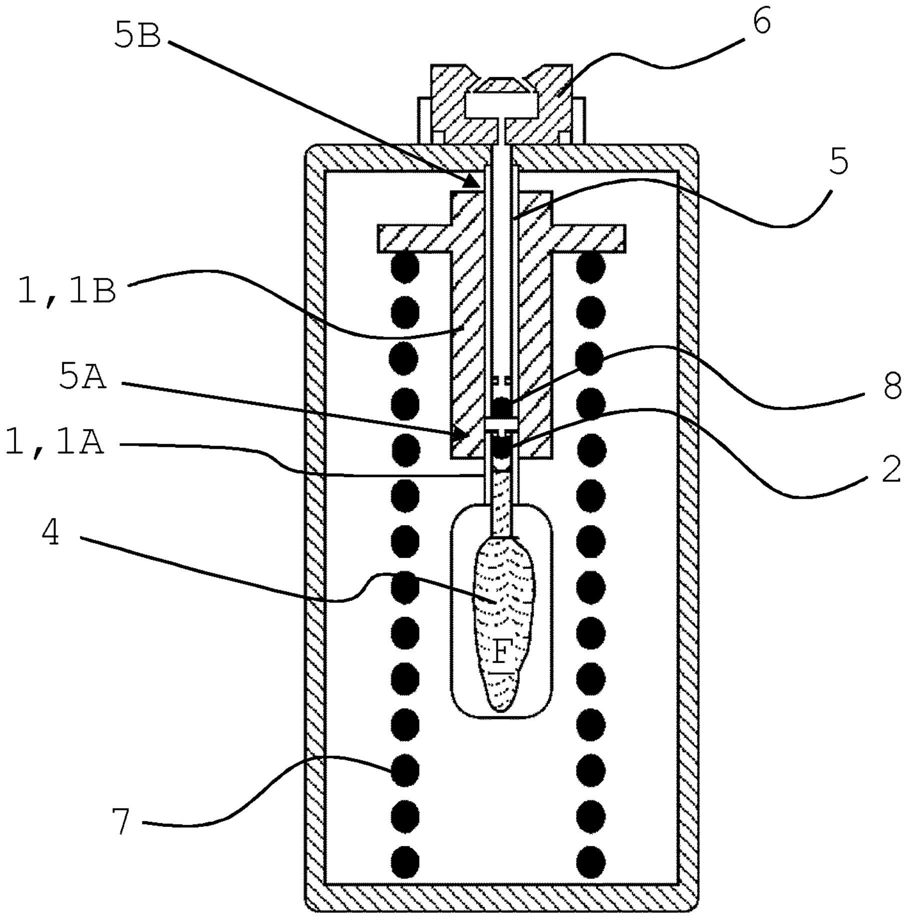
FIG. 1 shows a schematic view of some components of an inhalation device.

The inhalation device comprises a housing, inside this housing a reservoir 4 for storing a liquid F, and a pumping unit with a pumping chamber for generation of a pressure inside said pumping chamber. The pumping chamber is fluidically connected with the reservoir 4 via a tubular member 1. The device further comprises a riser pipe 5 which can be received with at least one reservoir-facing, interior end 5A in said pumping chamber, and a nozzle 6 which is connected liquid-tight to an exterior end 5B of the riser pipe 5. The pumping chamber volume (interior volume of the pumping chamber) is changeable by means of linear relative motion of the riser pipe 5 to the tubular member 1. Further, at an downstream end of tubular member 1, a valve 2 is present in order to keep liquid F from flowing contrary to the desired flow direction, i.e. towards nozzle 6. Another, optional valve 8 is located at the upstream end of riser pipe 5 in order to keep liquid from flowing back from nozzle 6 into the pumping chamber.

Further, a means for the storage of potential energy 7 is provided, which can be manually loaded, wherein the stored energy is releasable to said pumping unit when released by activation of a release means (not shown).

In this embodiment, the tubular member 1 can be regarded as comprising a first part 1A which provides, at its upstream end, the valve chamber for valve 2, and which further comprises a second part 1B, wherein riser pipe 5, serving as a counter piece, is least partially insertable into said second part 1B. In this embodiment, the diameter of first part 1A and second part 1B are not identical. FIG. 1 does not show that the first part 1A and the second part 1B form an interface section serving as a valve chamber for the valve 2.

Figure 2:
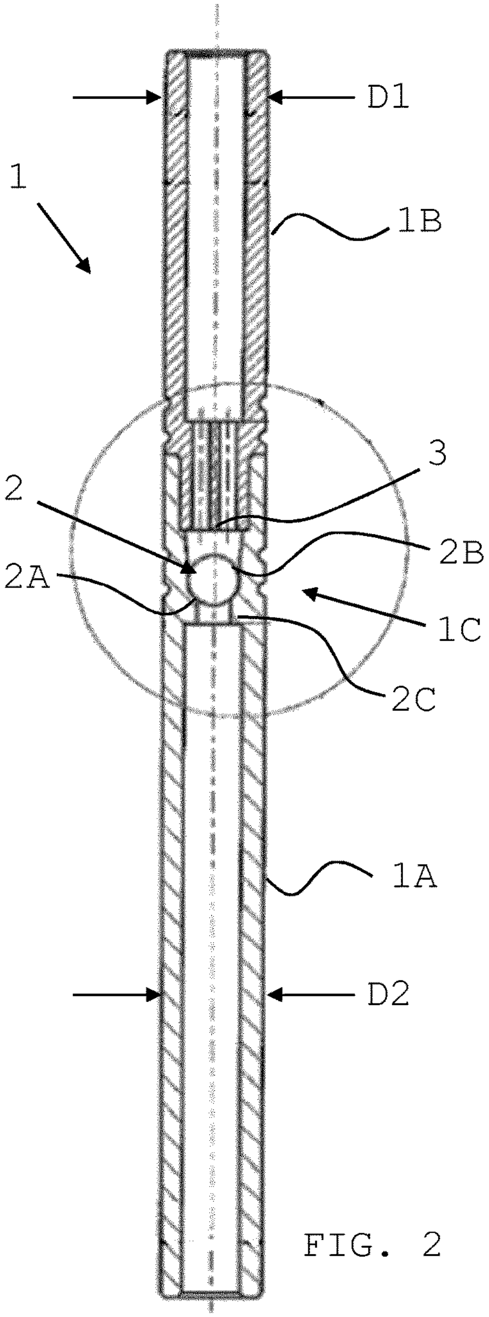
FIG. 2 shows one embodiment of a tube according to the invention in a cross sectional view.
Figure 3:
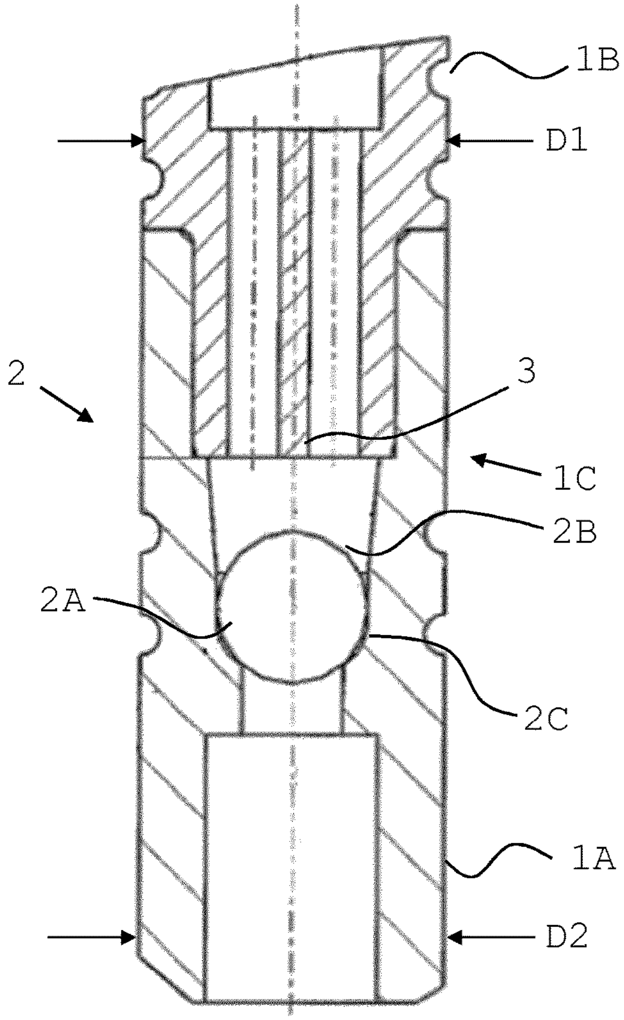
FIG. 3 shows a detail of the view of the embodiment of FIG. 2.

In FIG. 2, one preferred embodiment of a tubular member according to the invention is shown in a cross sectional view. FIG. 3 shows a more detailed view.

In said embodiment, the tubular member 1 which consists of a first part 1A and a second part 1B has, along its extension, an substantially identical diameter, since D1 is approximately equal to D2. Not shown are the reservoir 4 and the nozzle unit 6 to which the first and the second part can respectively be fluidically connected.

In the depicted embodiment, the first part 1A is configured to be in direct fluidic contact with said reservoir 4. In a not depicted embodiment, the first part 1A is configured to be connected to a further tube or flexible hose, and said further tube or hose can then be in direct or indirect fluidic connection with the reservoir 4. In such an embodiment, the first part 1A servers rather as an adapter part.

In analogy, the same can apply to the second part 1B which can also serve as an adapter part for a further tube for contacting the body of the pumping unit (hatched component in FIG. 1 around riser pipe 5). At the interface section 1C, a check valve 2 is present. In the depicted embodiment, this is a ball valve with a ball 2A located inside a valve chamber 2B.

In the depicted embodiment, the interface section 1C is part of the first part 1A. In a not depicted embodiment, the interface section 1C is part of the second part 1B.

The flow direction of the liquid (not shown) is from the bottom to the top in both FIGS. 2 and 3. Valve 2 which is a check valve ensures that no liquid can flow in the opposite direction.

The part which does not comprise the valve chamber 1C, which is part 1B in the depicted embodiment, has at its upstream end (in the picture, the lower end) a structure 3 for holding back the moveable part (ball 2A) of valve 2. Structure 3 consists of a surface with two through holes, each having an inner diameter which is significantly smaller than the diameter of ball 2A. Thus, ball 2A cannot leave valve chamber 2B in direction of the liquid flow (upwards in the picture). At the same time, liquid can pass ball 2A and flow through said holes. In the opposite direction, the valve seat 2C is present, which also blocks further movement of ball 2A, and which additionally seals against said back flow.

Both parts 1A and 1B can be pressed together in order to provide a sufficiently tight seal. While part 1B should be manufactured with higher precision since it slides into an out of the opening in the body of the pumping unit (not shown), the lower part 1A can be fabricated with less precision. Furthermore, the material of the first part 1A can be of a lower strength than the material of second part 1B since mainly, only part 1B is exposed to high pressures.

Figure 4:
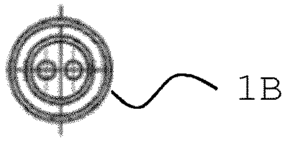
FIG. 4 shows a top view of the embodiment of FIG. 2.

In FIG. 4, the top view onto second part 1B is depicted, and the two through holes of structure 3 can be seen from the outside.

LIST OF REFERENCES

1 tubular member
1A first part
1B second part
1C interface section
2 valve, check valve
2A ball, moveable part
2B valve chamber
2C valve seat
3 structure
4 reservoir
5 riser pipe
5A interior end
5B exterior end
6 nozzle, nozzle unit
7 means for the storage of potential energy
8 valve
D1 diameter of first part
D2 diameter of second part

The invention claimed is:

1. Pumping unit for an inhalation device for medically active liquids for generation of an aerosol, wherein the pumping unit comprises a tubular member, a check valve, and a counter piece, said counter piece being configured to receive at least a downstream segment of said tubular member and having an interior volume, wherein upstream of said tubular member, a reservoir is directly or indirectly fluidically connected with said tubular member, and downstream of said counter piece, a nozzle unit is directly or indirectly fluidically connected with said counter piece, and wherein the tubular member comprises an upstream section, a downstream section, and the check valve which is positioned between the upstream section and the downstream section, such that a pumping chamber with a pumping chamber volume is defined which comprises the volume of the downstream section of the tubular member and optionally said interior volume of the counter piece, and wherein tubular member and the counter piece move relatively to one another, such that the pumping chamber volume is variable, characterized in that the tubular member comprises at least two mechanically distinct parts, wherein a first part provides said upstream section, and a second part provides said downstream section, and wherein the first part and the second part are connected to each other such as to form an interface section serving as a valve chamber for the valve, wherein the counter piece comprises a riser pipe which extends towards the second part of the tubular member and which is at least partially insertable into the second part of the tubular member; and wherein the riser pipe extends through a furthest downstream end of the second part of the tubular member.

2. Pumping unit according to claim 1, wherein the outside diameter of the first and the second part is substantially identical.

3. Pumping unit according to claim 1, wherein the outside diameters of the first and the second part differ from one another.

4. Pumping unit according to claim 1, wherein the first and the second part are made of different materials.

5. Pumping unit according to claim 1, wherein to the first part of the tubular member, more than one reservoir is directly or indirectly fluidically connected.

6. Inhalation device for medically active liquids for generation of an aerosol, comprising a pumping unit according to claim 1.

* * * * *